United States Patent
Shantha et al.

(10) Patent No.: US 12,214,131 B2
(45) Date of Patent: Feb. 4, 2025

(54) LOWER JAW AND TONGUE THRUSTING, ENDOTRACHEAL TUBE AND FLEXIBLE FIBEROPTIC ENDOSCOPE INTUBATION ORAL AIRWAY DEVICE

(71) Applicant: WEDGE THERAPEUTICS, LLC, St. Paul, MN (US)

(72) Inventors: Totada R Shantha, Stone Mountain, GA (US); Robert Wieden, St. Paul, MN (US)

(73) Assignee: WEDGE THERAPEUTICS, LLC, St. Paul, MN (US)

( * ) Notice: Subject to any disclaimer, the term of this patent is extended or adjusted under 35 U.S.C. 154(b) by 907 days.

(21) Appl. No.: 17/297,926

(22) PCT Filed: Nov. 27, 2019

(86) PCT No.: PCT/US2019/063638
§ 371 (c)(1),
(2) Date: May 27, 2021

(87) PCT Pub. No.: WO2020/113026
PCT Pub. Date: Jun. 4, 2020

(65) Prior Publication Data
US 2022/0023565 A1 Jan. 27, 2022

Related U.S. Application Data
(60) Provisional application No. 62/771,855, filed on Nov. 27, 2018.

(51) Int. Cl.
*A61M 16/04* (2006.01)
*A61B 1/00* (2006.01)
*A61B 1/24* (2006.01)

(52) U.S. Cl.
CPC ...... *A61M 16/0495* (2014.02); *A61B 1/00154* (2013.01); *A61B 1/00165* (2013.01); *A61B 1/24* (2013.01); *A61M 16/0493* (2014.02)

(58) Field of Classification Search
CPC ............ A61B 1/00147; A61B 1/00154; A61B 1/00163; A61B 1/00165; A61B 1/24;
(Continued)

(56) References Cited

U.S. PATENT DOCUMENTS 2,127,215 A    8/1938   Gwathmey
2,599,521 A    6/1952   Berman
(Continued)

FOREIGN PATENT DOCUMENTS

EP         3886955 B1    6/2023
WO    WO-9965553 A1 *   12/1999  ........ A61M 16/0488
(Continued)

OTHER PUBLICATIONS

Aoyama, Kazuyoshi et.al., Jaw Thrust Maneuver for Endotracheal Intubation Using a Fiberoptic Stylet. Anesthesia & Analgesia: Jun. 2000—vol. 90—Issue 6—p. 1457-1458.
(Continued)

*Primary Examiner* — Kendra D Carter
*Assistant Examiner* — Jaeick Jang
(74) *Attorney, Agent, or Firm* — Merchant & Gould P.C.

(57) ABSTRACT

A lower jaw and tongue thrusting endotracheal tube and flexible fiberoptic endoscope intubation oral airway device having an elongated body including, a mandible flange with a lingual flat portion transversely disposed on a ventral surface of a tongue plate. The device having an open top toward the palate like a rectangular trough. The trough extends through the device from the proximal end to the front middle part of the tongue plate. The device includes an L-shaped insert that slideably couples between the upper lip
(Continued)

flanges and acts also as dorsal surface of the bite block. The distal end of the tongue plate end comprises a curved surface which tapers to a narrow distal edge. A pair of upstanding walls attach to the tongue faceplate ventral surface edges which taper as they extend posteriorly. The walls ensure protection for medical instruments disposed within the flexible fiberoptic endoscope guide.

16 Claims, 8 Drawing Sheets

(58) Field of Classification Search
CPC ......... A61B 1/247; A61B 1/267; A61B 90/16; A61M 2205/0238; A61M 2205/588; A61M 16/0488; A61M 16/049; A61M 16/0493; A61M 16/0495; A61F 5/56; A61F 5/566
See application file for complete search history.

(56) References Cited

U.S. PATENT DOCUMENTS

| | | | |
|---|---|---|---|
| 2,705,959 A | 4/1955 | Elmore | |
| 3,013,554 A | 12/1961 | Safar et al. | |
| 3,057,347 A | 10/1962 | McGee | |
| 3,306,298 A | 2/1967 | Raimo | |
| 3,419,004 A | 12/1968 | Berman | |
| 3,543,751 A | 12/1970 | Sheffer | |
| 3,756,244 A | 9/1973 | Kinnear et al. | |
| 3,908,665 A | 9/1975 | Moses | |
| 3,930,507 A | 1/1976 | Berman | |
| 4,054,135 A | 10/1977 | Berman | |
| 4,067,331 A | 1/1978 | Berman | |
| 4,112,936 A | 9/1978 | Blachly | |
| D261,442 S | 10/1981 | Anderson | |
| 4,338,930 A | 7/1982 | Williams | |
| 4,363,320 A | 12/1982 | Kossove | |
| 4,365,625 A | 12/1982 | Rind | |
| 4,495,945 A | 1/1985 | Liegner | |
| 4,553,540 A * | 11/1985 | Straith | A61M 16/0495 128/207.14 |
| D284,701 S | 7/1986 | Deenadayalu | |
| 4,848,331 A | 7/1989 | Northway-Meyer | |
| 4,919,126 A | 4/1990 | Baildon | |
| 4,944,313 A | 7/1990 | Katz et al. | |
| 5,024,218 A | 6/1991 | Ovassapian et al. | |
| D318,124 S | 7/1991 | Siemsen | |
| 5,174,284 A | 12/1992 | Jackson | |
| 5,205,281 A | 4/1993 | Buchanan | |
| 5,413,095 A | 5/1995 | Weaver | |
| 5,590,643 A | 1/1997 | Flam | |
| 7,171,962 B1 | 2/2007 | Bloem | |
| 7,278,420 B2 | 10/2007 | Ganesh et al. | |
| 7,328,698 B2 | 2/2008 | Scarberry et al. | |
| 7,658,191 B2 | 2/2010 | Takuma | |
| 7,866,313 B2 | 1/2011 | Isenberg et al. | |
| 7,913,687 B2 | 3/2011 | Munn | |
| 7,946,289 B2 | 5/2011 | Munn | |
| 7,954,488 B2 | 6/2011 | Munn | |
| 7,975,695 B2 | 7/2011 | Munn | |
| 8,220,461 B1 | 7/2012 | Guerra et al. | |
| D680,642 S | 4/2013 | Guerra et al. | |
| 8,413,658 B2 | 4/2013 | Williams | |
| 8,485,194 B2 | 7/2013 | Guerra et al. | |
| D695,390 S | 12/2013 | Bruggeman et al. | |
| 8,640,692 B2 | 2/2014 | Matioc | |
| D701,962 S | 4/2014 | Chung | |
| 8,783,261 B2 | 7/2014 | Thornton | |
| 8,794,230 B2 | 8/2014 | Abrons | |
| 9,072,613 B2 | 7/2015 | Shantha | |
| 9,254,219 B2 | 2/2016 | Shantha | |
| 9,669,174 B2 | 6/2017 | Isenberg et al. | |
| D847,350 S | 4/2019 | Eaton | |
| 10,258,319 B2 | 4/2019 | Arden et al. | |
| D849,233 S | 5/2019 | Shantha et al. | |
| D849,234 S | 5/2019 | Shantha et al. | |
| 10,413,689 B2 | 9/2019 | Eaton et al. | |
| D885,558 S | 5/2020 | Shantha et al. | |
| 11,623,058 B2 * | 4/2023 | Shantha | A61B 1/00154 128/207.15 |
| 2003/0000534 A1 | 1/2003 | Alfery | |
| 2003/0131853 A1 | 7/2003 | Wall, Jr. et al. | |
| 2004/0129272 A1 | 7/2004 | Ganesh et al. | |
| 2008/0078402 A1 | 4/2008 | Mongeon | |
| 2008/0092882 A1 | 4/2008 | Munn | |
| 2008/0092900 A1 | 4/2008 | Munn | |
| 2008/0185004 A1 | 8/2008 | Munn | |
| 2008/0230054 A1 | 9/2008 | Prineas | |
| 2010/0132700 A1 * | 6/2010 | Filipi | A61B 1/00154 128/200.26 |
| 2010/0199998 A1 | 8/2010 | Matioc | |
| 2012/0048278 A1 | 3/2012 | Yasick | |
| 2012/0143003 A1 * | 6/2012 | Anca | A61M 16/0497 600/114 |
| 2012/0234331 A1 | 9/2012 | Shantha | |
| 2012/0234332 A1 | 9/2012 | Shantha | |
| 2012/0255561 A1 | 10/2012 | Shantha | |
| 2012/0283513 A1 | 11/2012 | Leeflang et al. | |
| 2013/0014754 A1 | 1/2013 | Guerra et al. | |
| 2014/0007868 A1 * | 1/2014 | Eaton | A61B 1/24 128/200.26 |
| 2014/0069421 A1 | 3/2014 | Kuo | |
| 2014/0323896 A1 | 10/2014 | McCauley | |
| 2014/0373849 A1 | 12/2014 | Akihiro | |
| 2015/0013672 A1 | 1/2015 | Abdoue | |
| 2016/0022129 A1 | 1/2016 | Colman et al. | |
| 2016/0206303 A1 | 7/2016 | Chaudhry et al. | |
| 2017/0000641 A1 | 1/2017 | Arden et al. | |
| 2017/0203067 A1 | 7/2017 | Eaton et al. | |
| 2017/0266401 A1 * | 9/2017 | Arden | A61B 17/025 |
| 2018/0085545 A1 | 3/2018 | Maslow | |
| 2018/0311455 A1 * | 11/2018 | Simons | A61M 16/0497 |
| 2021/0213225 A1 * | 7/2021 | Wallis | A61B 1/01 |

FOREIGN PATENT DOCUMENTS

| | | | |
|---|---|---|---|
| WO | WO-2007048884 A1 * | 5/2007 | ........ A61M 16/0488 |
| WO | 2017/006117 A1 | 1/2017 | |
| WO | 2017/197498 A1 | 11/2017 | |
| WO | 2018/200063 A1 | 11/2018 | |
| WO | 2020/113026 A1 | 6/2020 | |

OTHER PUBLICATIONS

Apfelbaum JL, Hagberg CA, Caplan RA, Blitt CD, Connis RT, Nickinovich DG, et al. Practice guidelines for management of the difficult airway: an updated report by the American Society of Anesthesiologists Task Force on Management of the Difficult Airway. Anesthesiology 2013;118:251-270.

Chang, Jee-Eun et.al., Effect of Jaw Thrust on Transesophageal Echocardiography Probe Insertion and Concomitant Oropharyngeal Injury. Journal of Cardiothoracic and Vascular Anesthesia, 29, 5, 2015, pp. 1266-1271.

Crawford, MW, et al., Effect of propofol anesthesia and continuous positive airway pressure on upper airway size and configuration in infants. Anesthesiology 2006:105:45-50.

Crawford, MW, et al., Extent and localization of changes in upper airway caliber with varying concentrations of sevoflurane in children. Anesthesiology 2006:105:1147-1152.

Dickinson, Ed; Limmer, Dan; O'Keefe, Michael F.; Grant, Harvey D.; Murray, Bob (2008). Emergency Care (11th Edition). Englewood Cliffs, N.J: Prentice Hall. pp. 157-159.

Drummond, GB, Influence of thiopentone on upper airway muscles. British Journal of Anaesthesia 1989:63:12-21.

Eastwood, PR, et al., Collapsibility of the upper airway at different concentrations of propofol anesthesia. Anesthesiology 2005:103:470-477.

Eastwood, PR, et al., Collapsibility of the upper airway during anesthesia with isoflurane. Anesthesiology 2002; 97:786-793.

(56) References Cited

OTHER PUBLICATIONS

Hwang, JC, et al. Respiratory-related hypoglossal nerve activity: influence of anaesthetics. Journal of Applied Physiology 1983; 55:785-792.
Inazawa, T., et al., Effect of manibular position on upper airway collapsibility and resistance. J Dent Res 2005;84:554-558.
International Search Report Mailed Apr. 24, 2020 PCT/US2019/063638.
International Search Report Mailed May 9, 2018 PCT/US2018/017812.
Isono, S., et al., Advancement of the mandible improves velopharyngeal airway patency. J Appl Physiol 1995; 79:2132-2138.
Isono, S., Optimal combination of head, mandible and body positions for pharyngeal airway maintenance during perioperative period: Lesson from pharyngeal closing pressures. Semin Anesth Periop Med Pain 2007; 26:83-93.
Isono, S., et al. Pharyngeal patency in response to advancement of the mandible in obese anesthetized persons. Anesthesiology 1997; 87:1055-1062.
Isono, S. et al., Sniffing position improves pharyngeal airway patency in patients with obstructive sleep apnea. Anesthesiology 2005; 103:489-494.
Joffe, Aaron M. et al., A Two-handed Jaw-thrust Technique Is Superior to the One-handed "EC-clamp" Technique for Mask Ventilation in the Apneic Unconscious Person. Anesthesiology 2010; 113:873-9.
Kato, J. et al., Dose-dependent effects of mandibular advancement on pharyngeal mechanics and nocturnal oxygenation in patients with sleep disordered breathing. Chest 2000; 117:1065-1072.
Kheterpal, S. et al., Incidence and Predictors of Difficult and Impossible Mask Ventilation. Anesthesiology 2006: 105:885-891.
Kheterpal, S. et al., Prediction and outcomes of impossible mask ventilation: A review of 50,000 anesthetics. Anesthesiology 2009: 110:891-897.
Kitagawa H, Yamazaki T, Imashuku Y. The "jaw thrust" maneuver rather than the "BURP" maneuver improves the glottic view for Pentax-AWS assisted tracheal intubation in a patient with a laryngeal aperture. Can J Anaesth 2010;57:517-518.
Kuna, Samuel T. et al., Effect of nasal airway positive pressure on upper airway size and configuration. Am Rev Respir Dis 1988; 138:969-975.
Kuna, Samuel T. et al., Effects of progressive mandibular advancement on pharyngeal airway size in anesthetized adults. Anesthesiology 2008; 109:605-612.
Kuna, Samuel T. et al., Evaluation of an oral mandibular advancement titration appliance. Oral Surg Oral Med Oral Pathol Oral Radiol Endod 2006; 101:593-603.
Langeron, et al., Prediction of difficult mask ventilation. Anesthesiology 2000: 92:1229-1236.
Lee, AR, et al., A comparison of the BURP and conventional and modified jaw thrust manoeuvres for orotracheal intubation using the Clarus Video System. Anaesthesia 2013;68: 931-937.
Liang, Y, et al., Nasal ventilation is more effective than combined oral-nasal ventilation during induction of general anesthesia in adult subjects. Anesthesiology 2008; 108:998-1003.
Litman, Ronald S., Upper airway collapsibility: an emerging paradigm for measuring the safety of anesthetic and sedative agents. Anesthesiology 2005; 103:453-454.
Litman, Ronald S., et al., Use of dynamic negative airway pressure (DNAP) to assess sedative-inducted upper airway obstruction. Anesthesiology 2002; 96:342-345.
Mallampati et al., Clinical sign to predict difficult tracheal intubation: a prospective study; Canadian Anaesthetists' Society Journal 1985; 32:4; 429-434.
Mathru M, et al., Magnetic resonance imaging of the upper airway; Effects of propofol anesthesia and nasal continuous positive airway pressure in humans. Anesthesiology 1996; 84:273-279.
Meier S, et al., The effect of chin lift, jaw thrust, and continuous positive airway pressure on the size of the glottic opening and on stridor score in anesthetized, spontaneously breathing children. Anesth Analg 2002; 94:494-499.
Morikawa S, et al., Influence of headjaw position upon upper airway patency. Anesthesiology 1961; 22:265-270.
Murashima K, Fukutome T. Effect of jaw-thrust maneuver on the laryngeal inlet. Anaesthesia 1998; 53:203-204.
Nandi PR, et al., Effect of general anesthesia on the pharynx. Br J Anaesth 1991; 66:157-162.
Norton JR, et al., Differences between midazolam and propofol sedation on upper airway collapsibility using dynamic negative airway pressure. Anesthesiology 2006; 104:1155-1164.
Ochiai R, et al., Effects of varying concentrations of halothane on the activity of the genioglossus, intercostals and diaphragm in cats: An electromyographic study. Anesthesiology1989; 70:812-816.
Reber A, et al., Effect of common airway manoeuvres on upper airway dimensions and clinical signs in anaesthetized, spontaneously breathing children. Br J Anaesth 2001; 86:217-222.
Reed WR, et al., Factors influencing regional patency and configuration of the humaninfant upper airway. J Appl Physiol 1985; 58:635-644.
Safar P, et al. A comparison of the mouth to mouth and mouth-to-airway methods of artificial respiration with the chest-pressure arm-lift methods. N Engl J Med 1958; 258:671-677.
Safar P, et al. Upper airway obstruction in the unconscious patient. J Appl Physiol 1959; 14:760-764.
Sivarajan M, et al. Effects of general anesthesia and paralysis on upper airway changes due to head position in humans. Anesthesiology 1996; 85:787-793.
Sivarajan M, et al. The position and the state of the larynx during general anesthesia and muscle paralysis. Anesthesiology 1990; 72:439-442.
Stacey MR, et al., A comparison of direct laryngoscopy and jaw thrust to aid fibreoptic intubation. Anaesthesia 2005; 60:445-448.
Tagaito Y, et al., Lung volume and collapsibility of the passive pharynx in patients with sleep-disordered breathing. J Appl Physiol 2007; 103:1379-1385.
Tsuiki S, et al., Anatomical balance of the upper airway and obstructive sleep apnea. Anesthesiology 2008; 108:1009-1015.
Uzun L, et al., Effectiveness of the jaw-thrust maneuver in opening the airway: A flexible fiberoptic endoscopic study. ORL J Otorhinolaryngol Relat Spec 2005; 67:39-44.
Weiser TG et al., Size and distribution of the global volume of surgery in 2012, Bulletin of the World Health Organization2016; 94:201-209F.
Whittingham H, Discussion on Artificial Respiration. Proc R Soc Med. May 1960; 53(5): 311-316.
Yang Seong-Mi et.al., A comparison of single-handed chin lift and two-handed jaw thrust for tracheal intubation using a lightwand. Journal of Anesthesia. Feb. 2017, vol. 31, Issue 1, pp. 5-10.
Nishino T, Shirahata M, Yonezawa T, Honda Y. Comparison of changes in the hypoglossal and phrenic nerve activity in response to increasing depth of anesthesia in cats. Anesthesiology 1984; 60:19-24.
Weiser et al., An estimate of global volume of surgery; Lancet 2008; 372: 139-44.
Anesthesiologists Task Force, Practice Guidelines for Management of the Difficult Airway, Anesthesiology May 2003, vol. 98, 1269-1277.
Superior Oral Air ways that Actually Open the Oropharyngeal Air way. Wedge Therepeutics. Web archive date: Mar. 29, 2018. Retrieved from Internet: <https://web.archive.org/web/20180329221933/ http://wedgetherapeutics.com/> (Year: 2018).
Wieden, Bob: Therapeutic Focus—A New Patented Device for Treating Obstructive Sleep Apnea & Snoring; Journal of Drug Development & Delivery. Jun. 2017, vol. 17, # 5, pp. 68-71.
Guedel, A. E., A Nontraumatic Pharyngeal Airway, J. Am. Med. Assoc., Jun. 10, 1933, vol. 100, p. 1862.
Supplementary European Search Report Mailed Dec. 2, 2021 EP 20190890978.

* cited by examiner

LOWER JAW AND TONGUE THRUSTING, ENDOTRACHEAL TUBE AND FLEXIBLE FIBEROPTIC ENDOSCOPE INTUBATION ORAL AIRWAY DEVICE

RELATED APPLICATION

The present application claims the benefit of U.S. Provisional Application No. 62/771,855 entitled LOWER JAW AND TONGUE THRUSTING, ENDOTRACHEAL TUBE AND FLEXIBLE FIBEROPTIC ENDOSCOPE INTUBATION ORAL AIRWAY DEVICE, filed Nov. 27, 2018, said application being hereby incorporated herein by reference in its entirety.

TECHNICAL FIELD

This disclosure relates generally to oral airway devices for administration on patients undergoing surgical procedures to open and maintain the oropharyngeal airway passage of a patient during the procedures. More specifically, this disclosure relates to lower jaw and tongue thrusting oropharyngeal airway devices for medical use on persons under anesthesia, in unconscious or semi-conscious states, or under topical anesthesia to maintain an open airway. These devices can aid in placement of a flexible fiberoptic endoscope for esophagogastroduodenoscopy and laryngo-trachea-bronchoscopy. These devices can also be used in difficult intubations to place an endotracheal tube for breathing and administration of anesthesia and oxygen.

Various embodiments of the disclosed oral airway device can be abbreviated as an LJT-ET-FO oral airway device, which is short for a Lower Jaw and Tongue Thrusting (LH) Endotracheal Tube (ET) and Flexible Fiberoptic Endoscope (FO) Intubation oral airway device.

Accordingly, devices described can include LJT-ET-FO oral airway devices that can be used for any number of medical conditions and fiberoptic procedures of upper airways. This allows esophageal access for esophagogastroduodenoscopy (EGD) and other endoscopic procedures and for ET intubation in patients with difficult or potentially difficult intubation. Specifically, various embodiments disclosed herein relate to LJT, mandibular protracting, tongue root pulling forward, opening up the oral and oropharynx airways for easy access by fiberoptic endoscopic devices.

Devices sometimes referred to as "LJT-ET-FO oral airway devices", "oropharyngeal airway devices", "oropharyngeal airways", "oral airways", "oral airway devices", and similar devices will generally be referred to broadly throughout this disclosure using the generic term "oral airway device".

SUMMARY

Embodiments relate to oral airway devices adapted to facilitate tracheal intubation with the help of a flexible fiberoptic endoscope and are used for EGD in awake, sedated, and anesthetized patients. Embodiments include oral airway devices that prevent the jaw and the tongue from falling back by pulling the root of the tongue away from the epiglottis and pharyngeal wall, that make the oral and oropharynx air passage wide open for easy exchange of gases, that extend the fauces open, that prevent any chance of the tongue obstructing the oropharynx-naso-pharynx air passage, that facilitate the insertion of fiberoptic scopes used for diagnosis, and that facilitate intubation when faced with difficult patient airways for surgery.

Embodiments relate to oral airway devices adapted to function as a guide and passageway for flexible fiberoptic endoscope insertion for laryngoscopy, bronchoscopy, EGD, and placing medical devices such as endotracheal tubes for the intubation of a human larynx and trachea.

Embodiments relate to a lower jaw and tongue thrusting endotracheal tube and flexible fiberoptic endoscope intubation oral airway device. The oral airway device includes an elongate member having a distal end and a proximal end. The elongate member is sized for insertion in the mouth of a patient and facilitation of air and medical instrument passage between the proximal and distal ends. The elongate member generally includes a flange assembly, a tongue plate, a trough and a mandibular flange. The flange assembly is located at the proximal end of the elongate member and includes a lower lip flange, a pair of upper lip flanges, and a sliding insert that removably couples the pair of upper lip flanges. The sliding insert includes a maxillary engagement surface that defines an upper cover of a passageway that extends into the elongate member. The tongue plate extends to the distal end of the elongate member and the trough extends between the flange assembly and the tongue plate. The mandibular flange projects downwardly and is transversely disposed at a first proximal end of the trough. The mandibular flange has a proximally facing surface that is located proximal to the maxillary engagement surface of the sliding insert but distal to the lower lip flange.

Embodiments relate to a lower jaw and tongue thrusting endotracheal tube and flexible fiberoptic endoscope intubation oral airway device. The oral airway device includes a semi-rigid, semi-rectangular, elongate member with two lateral walls extending from a flat ventral base with an open top lumen. The elongate member extends from a proximal end that includes an upper lip flange, a lower lip flange, and a bite block to a distal end having structure for location adjacent the root of the tongue of a patient including a tongue plate. The bite block partially defines a passageway between a pair of spaced apart lip flange projections that comprise the upper lip flange and the lower lip flange. The bite block has a ventral surface with a mandibular flange at the level of the upper lip flange in vertical alignment. The mandibular flange is configured to be placed behind mandibular incisor teeth of the patient to hold the lower mandibular jaw and the tongue of the patient as the lower jaw is thrust forward into position. Further, the bite block has a resilient, teeth and lip engaging part on the ventral surface between the lower lip flange and the mandibular flange for placing lower incisor teeth and lower lip for maintaining a protracted mandibular position.

Embodiments relate to a lower jaw and tongue thrusting endotracheal tube and flexible fiberoptic endoscope intubation oral airway device. The oral airway device includes an elongate member having a distal end and a proximal end defining an air passageway channel there between. The elongate member is sized for insertion in a patient's mouth such that the distal end is disposed adjacent the patient's tongue root while the proximal end remains disposed outside the patient mouth in front of the lips. The elongate member includes a plurality of lip flanges located at the proximal end of the elongate member, each having an outwardly projecting surface configured to overlie lips of the patient and located around an exit airway opening, with two segments having side locations. The elongate member includes a curved main body extending to the distal end of the elongate member for holding the tongue of the patient pressed downwards and inferiorly to prevents its backward movement. The elongate member includes a bite block disposed between the plurality of lip flanges and the curved main body, including an upper dorsal surface having a first bite location for maxillary incisor teeth engagement and a lower ventral surface having a second bite location for mandibular incisor teeth engagement. Further, the lower ventral surface of the bite block includes a mandibular flange projecting downwards, located distal to the second bite location for mandibular incisor teeth engagement.

For maintenance of a safe general anesthesia for prolonged periods repeatedly, it is necessary to intubate the trachea of the patient to permit the safe passage of oxygen and anesthesia gases into and out of the lungs of the patient and prevent aspiration of regurgitants. Oral airway devices are utilized to prevent the tongue of a patient from falling back into the throat and obstruction of the flow of air into the lungs, as for example, in an unconscious patient and when an anesthetic is being administered to the patient.

In general, oral airway devices are medical airway adjunct devices used to open and maintain the oropharyngeal airway passage of a patient. Oral airway devices act by preventing the tongue from moving posteroinferiorly towards the pharyngeal wall, and from covering the epiglottis, which could prevent the person from breathing by blocking the oropharynx air passage, which in turn, will block the naso-laryngo-pharynx air passages. When a person becomes unconscious, the muscles in the jaw connected to tongue movement and tongue muscles, become flaccid due to the loss of tone. The loss of tone of the genioglossus muscle (prime tongue protruding muscle) that results in the tongue moving posteriorly and inferiorly with the retraction of the mandible, resulting in the tongue obstructing the oropharyngeal air passage.

Oral airway devices are simple devices used millions of times (an estimated 350-400 million oral airways used annually) every year all over the world to establish an unobstructed ventilator air passage of the mouth in unconscious or semi-conscious patients or during CPR and other emergency situations as well as during EGD. Patients for EGD are performed under sedation mainlining the spontaneous breathing.

Each year in the United States, there are more than 15 million colonoscopies and 7 million upper-GI fiberoptic endoscopies, known as esophagogastroduodenoscopies, or EGDs are performed (besides >50 millions of anesthetics for general surgery) under sedation and/or anesthesia with spontaneous breathing with oral airway preventing the oral and oropharynx obstruction. Both colonoscopies and EGDs are performed with an endoscope, a reusable optical instrument that allows an endoscopist access to the gastrointestinal tract of a patient. They can be used to screen for disease or to perform a number of procedures, such as polyp removal, without the need for invasive surgery. Millions of fiberoptic procedures through the oral passage of the upper airways are performed, allowing the esophageal accesses for EDG and other endoscopic procedures as well as examination of the larynx and for endotracheal tube intubation in patients with difficult or potentially difficult intubation worldwide.

Resolution World Health Assembly (WHA68.15) resolved that strengthening emergency and essential surgical care and anesthesia as a component of universal health coverage, making the use of proper oral airway during these procedures described herein (Sixty-eighth World Health Assembly, Geneva, 18-26 May 2015. Geneva: World Health Organization; 2015). The present increase in surgery is 38% over the previous eight years.

The oral airway devices in use at present lack a mandibular protracting jaw-thrusting effect, that is needed to pull the tongue, with its genioglossus muscle forward, thus pulling the tongue away from the oropharynx, and thus preventing the blocking of the oropharynx airway and collapse of the fauces. For example, the current Guedel and Berman airways that are being commonly employed do not prevent such an oropharynx and oral obstruction.

Applicant previously introduced the LH oral airway device to prevent unwanted jaw and tongue movement and corresponding oral airway obstruction. See PCT Patent Publication No. WO2018/200063 which is hereby incorporated by reference in its entirety. By pulling the tongue with the attached genioglossus muscle and by using a mechanical lower jaw-thrust incorporated in the LH oral airway devices, the palatoglossal muscle is taut and prevents the collapse of the fauces that can contribute to fauces collapse and to oropharyngeal airway blockage, if the lower jaw is not protracted.

Still, the previous LH oral airway device of Applicant, and other existing oral airway devices, were generally not suitable for fiberoptic procedures of upper airways, bronchoscopies, and allowing the esophageal access for EGD to examine the lining of the esophagus, stomach, and duodenum, as well as other upper GI endoscopic procedures and for endotracheal tube intubation in patients with difficult or potentially difficult intubation and for flexible fiberoptic intubation. For example, prior Guedel and Berman oral airway devices do not allow for fiber optic devices to be used. Even the specially designed Ovassapian and William's oral airway devices will not open the oral and oropharynx airway. The tongue can also create problems during insertion of the fiber optic scope since it is really not suited for intubation using fiber optic laryngoscopes. During a procedure, it is important to keep open the naso-oro-laryngo-pharynx air passages needed for the unobstructed entry of air into the laryngo-tracheobronchial air passages and lung alveoli as a patient breathes or is ventilated artificially by mask. Past oral airway devices do not sufficiently provide for this unobstructed arrangement.

Applicants have now further developed a new LH oral airway device that facilitates flexible fiberoptic endoscope and endotracheal tube placement. Further, when using the intubating oral airway device for fiberoptic intubation, it is also necessary, to insert a suction catheter into the pharynx of the patient for removal of phlegm, blood, saliva, and regurgitants. Insertion of a suction catheter is accommodated by the presently disclosed oral airway device.

Each of the following prior art U.S. patent references disclose conventional oral airway devices or related features: U.S. Pat. No. 5,024,218 to Ovassapian et al; U.S. Pat. No. 4,338,930 to Williams; U.S. Pat. Nos. 4,067,331, 4,054, 135, and 3,930,507 to Berman; U.S. Pat. No. 3,756,244 to Kinnear et.al.; U.S. Pat. No. 4,848,331 to Northway-Meyer; U.S. Patent Publication No. 2003/0000534 to Alfery; U.S. Pat. No. 7,913,687 to Munn; U.S. Pat. No. 8,485,194 to Guerra et al.; U.S. Pat. No. 9,669,174 to Isenberg et al.; U.S. Pat. No. 5,590,643 to Flam; U.S. Pat. No. 4,363,320 to Kossove; U.S. Pat. No. 4,919,126 to Baildon; U.S. Pat. No. 7,278,420 to Ganesh et al.; U.S. Pat. No. 8,413,658 to Williams; U.S. Pat. No. 4,944,313 to Katz et al; U.S. Pat. No. 5,174,284 to Jackson; and U.S. Pat. No. 5,413,095 to Weaver. Each of these U.S. patent references is hereby incorporated herein by reference. None of these oral airway devices incorporates a mandibular protracting jaw-thrusting embodiment which can be important to maintain the oro-naso-pharyngeal-laryngeal airway for ventilation to supply needed oxygen.

Guedel first described his oral airway device in 1933, when he published a small note in JAMA about how to maintain the airway in unconscious and semiconscious subjects using his device. Essentially all other oral airway devices that were introduced after Guedel followed the basic design and function of this first oral airway device. This oral airway device triggered many modifications with dozens of patents.

Some early devices incorporate on one side, a sidewall having a first opening or cut-away section that extends the entire length of the oral airway device and, on the other side, a sidewall having a second opening or cut-away section that generally extends along the midsection of the oral airway. Applicants recognize that these type of oral airway devices can be generally very narrow and unstable and include a posterior curve that tends to direct a fiber-optic scope and endotracheal tube posteriorly toward the esophagus instead of anteriorly toward the trachea. Further, Applicants recognize that a patients tongue may be able to override this type of device on one side or the other.

Other commercially available oral airway devices include a posterior pharyngeal curve that tends to direct a fiber-optic scope and endotracheal tube anteriorly toward the trachea. Applicants recognize that these oral airway devices can be very narrow and wobble in a patient's mouth, thereby making the fiber-optic scoping process difficult and oral airway cumbersome to remove without disrupting placement of an endotracheal tube after the endotracheal tube has been properly positioned with respect to the trachea.

Other commercially available oral airway devices include designs with a wide, flat lingual surface that allows for stability of the oral airway and forward depression of the tongue. Applicants recognize that these types of oral airway devices tend to direct the fiber-optic scope and endotracheal tube posteriorly toward the esophagus rather than anteriorly toward the trachea. It is also recognized that these types of devices can be very difficult to remove without disrupting placement of an endotracheal tube after the endotracheal tube has been properly positioned with respect to the trachea.

A variety of laryngeal oral airway devices exist for intubating and endoscopic procedures. In general, applicants recognize that these devices do not provide a simple airway for the protrusion of the lower jaw which maintains a large oropharynx passage airway for unobstructed ventilation and for the use of fiber optic and other scopes.

Applicants recognize that other existing oral airway devices do not protract the mandible with the tongue, and have the same shortcomings explained and are not suited for unobstructed ventilation and for the use of fiber optic scopes for intubation and for use during EGD procedures.

Applicants recognize that other devices are incapable of: protracting the mandible relative to the maxilla, maintaining the mandible in the protracted condition, or are too complicated for everyday use.

Other devices exist having a mouthpiece with oxygen receiving and directing structure with two nasal cannula connectors. However, Applicants recognize that despite the development of these approaches to connecting nasal cannula, none of these approaches teach how to efficiently integrate connecting a nasal cannula with an oral airway device having both a completely separate suction conduit and a breathing conduit.

The prior art oral airway devices mentioned above and otherwise are numerous. Among other deficiencies, they do not thrust the mandible and tongue forwards as our described in applicant's present and past patent application disclosures. Accordingly, the prior art insufficiently: prevents the tongue moving back, prevents the fauces from collapse, and keeps the oropharynx airway open and at the same time facilitates the fiberoptic procedures through the oral cavity.

Embodiments of LJT-ET-FO oral airway devices disclosed are adapted to facilitate tracheal intubation with the help of a flexible fiberoptic endoscope, flexible fiberoptic bronchoscopies and used for EGD in both awake, sedated and anesthetized patients. The oral airway device is designed to protect a fiberoptic endoscope and an endotracheal tube from damage by the teeth of a patient, and to maintain itself in a midline position.

Embodiments of this LJT-ET-FO oral airway device have an elongated body, lip flanges, and sliding platform which can act as support for the bite block and upper incisor teeth, and a C-shaped quadrangular tongue depressing feature.

In an embodiment, the proximal end has proximal upper lip flanges which are separated at the center to communicate with the main exit opening and lower lip flange connected to the bite block.

In an embodiment, the upper lip flange has a square opening, which accommodates a sliding L-shaped insert that can be affixed or removed and that can act as part of the bite block to prevent the biting of the flexible fiberoptic endoscope or endotracheal tube.

In an embodiment, the upper and lower lip flanges are connected by right and left extensions which will cover the lips on the side of proximal end to prevent any air leakage from the side of the oral airway device.

In an embodiment, the upper and lower lip flanges have a hole that communicates with the bite block and the C-shaped tongue plate extension connected to the posterior end of the bite block.

In an embodiment, the upper and lower lip flanges are connected around a central oval or square shaped air and oxygen entry and exit hole that communicates with bite block trough and the C-shaped tongue extension plate connected to the posterior end of the bite block. The center part of the upper lip flange is open and closed with a sliding L-shaped sliding hinge to facilitate the introduction of a flexible fiberoptic endoscope and endotracheal tube and facilitate the removal of the oral airway device with ease with fiber optic scope and endotracheal tube still in position if necessary.

In an embodiment, the ventral surface of the bite block is provided with a mandibular flange at the level of the upper lip flange, convex forwards to accommodate the incisor teeth and gum, and at the same time pulls the lower jaw forward with the tongue to open the oral and oropharynx airway to facilitate the flexible fiberoptic endoscope and endotracheal tube insertion into the larynx, and facilitates the guiding of the EGD flexible fiberoptic endoscope.

In an embodiment, the ventral surface of the bite block slants downwards inferiorly towards the lower front lip flange upper edge which allows to better hold and protract the mandibular teeth and jaw, which is caused by the flaccid jaw and tongue muscles relaxed under sedation, during and after anesthesia, thus prevents the jaw retracting downward and backwards from the jaw plane due to gravity and the patient being in a supine position.

In an embodiment, the distal end of the bite block is connected to an elongated square or U-shaped trough like tongue holding body. This curved lingual portion which is wider at its point of junction with the proximal half of the elongated body, narrowing down and becoming flat at its distal most end of the oral airway device.

In an embodiment, the lingual plate portion comprises a curve so as to permit an endotracheal tube and fiberscope scope tips to be directed towards the patient's larynx and esophageal opening.

In an embodiment, the oral airway device has a pair of walls upstanding from the sides on its proximal half of the device extending anteriorly from the lip flanges.

In an embodiment, the ventral surface of the tongue plate has at least three transverse elevated ridges to prevent the tongue slipping backwards during fiberoptic procedures.

In an embodiment, the ventral surface of the tongue plate of the tongue base is slightly curved to be convex, with the outer edges cuffed to present a ridge, to control the tongue from moving side-to-side.

In an embodiment, the ventral surface of the tongue plate also has an elevated nub occupying the center of the tip tongue plate to pull the root of the tongue away from the oropharynx and to extend open the oropharynx to facilitate the guiding of the tip of the fiberoptic scope to the laryngeal or esophageal openings.

In an embodiment, this fiberoptic procedure and intubating oral airway device is designed to accommodate an endotracheal tube with a balloon while being directed to the larynx and trachea with the help of a flexible fiberoptic endoscope without any impediment.

In an embodiment, the oral airway device provides expanded oral and oropharyngeal space for mask ventilation before tracheal intubation after induction of anesthesia or sedation and before insertion of flexible fiberoptic endoscope and endotracheal tube on flexible fiberoptic endoscope.

In an embodiment, due to the generally flat nature of the endoscope facilitating oral airway device, suctioning of the mouth is possible when the oral airway device is in place, with the patient lying on their back or sitting up.

In an embodiment, the oral airway device has a wide lingual surface to keep the patient's tongue away from the oropharynx inserted endoscope.

In an embodiment, the lateral wall of the oral part and bite block of the oral airway device is modified to provide a lateral canal to accommodate a laryngeal mask airway (LMA), if it is used to ventilate during the prolonged use of EDG instead of an endotracheal tube.

Various embodiments provide a novel approach to prevent the tongue from moving, while at the same time pulling it forwards to provide more space at the oropharynx for instrumentation and placement of other devices.

In an embodiment, the LJT-ET-FO oral airway device is designed to protect the fiberoptic endoscope and endotracheal tube from damage by the clamping of the patient's teeth, and to maintain itself in a midline position.

In an embodiment, the lingual portion curves so as to permit an endotracheal tube and fiberscope to be on a posterior plane and the lateral plane, a capability not realized by other past oral airway devices, which is further facilitated by protraction of the jaw by mandibular flange.

Embodiments of the LJT-ET-FO oral airway device permit simultaneous administering of anesthetics, oxygen, and suctioning.

Embodiments of the LJT-ET-FO oral airway device may be made from suitable medical materials, including plastic and semisynthetic materials.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1:
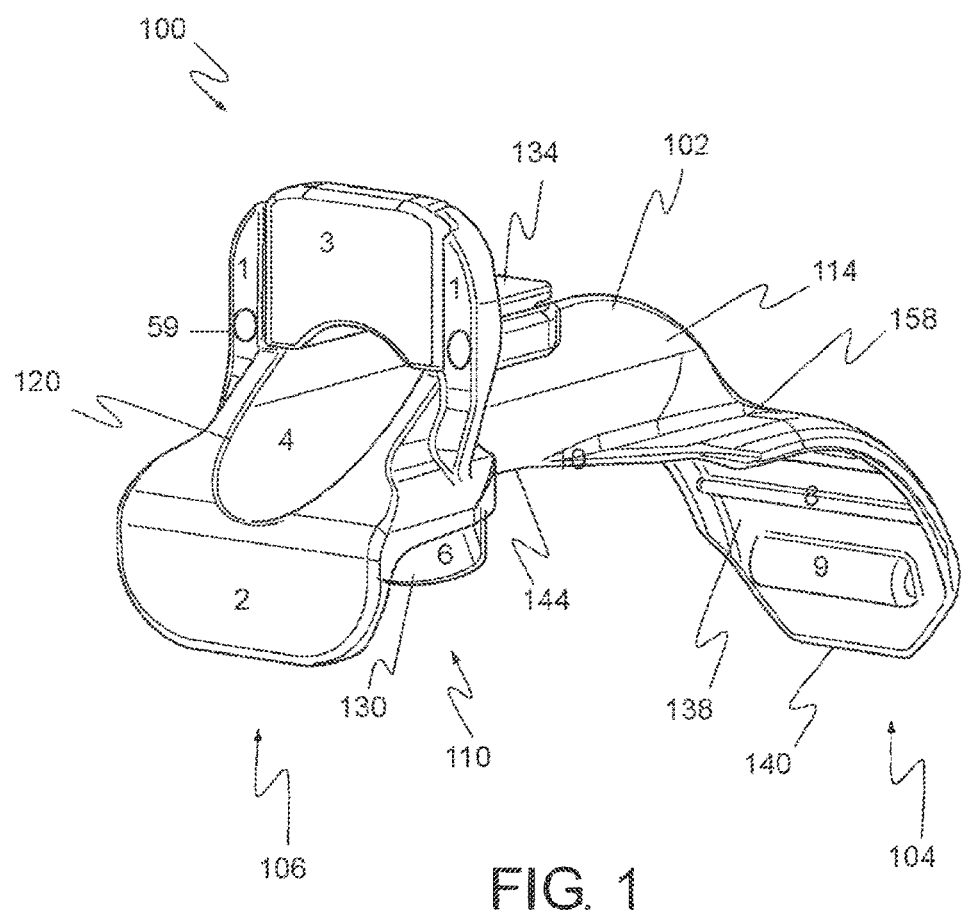
FIG. 1 is a front perspective view of an LJT-ET-FO oral airway device, according to an embodiment.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

Embodiments of oral airway devices described herein are generally LJT-ET-FO oral airway devices adapted to facilitate endotracheal intubation including access for a flexible fiberoptic endoscope, for EGD in awake, sedated, anesthetized and topicalized patients, and for use during laryngoscopy and bronchoscopy. Embodiments of the present oral airway device generally prevent the jaw and the tongue from falling back by pulling the root of the tongue away from the epiglottis and pharyngeal wall, making the oral and oropharynx air passage wide open for easy exchange of gases, by opening the fauces, and preventing the tongue from obstructing the oropharynx-naso-pharynx air passage and facilitating the insertion of fiberoptic scopes used to diagnose and to facilitate intubation when faced with difficult oral airways in procedures or surgery.

FIGS. 1-6 depict various views of an oral airway device 100. Oral airway device 100 is an LJT-ET-FO oral airway device adapted to facilitate tracheal intubation requiring a flexible fiberoptic endoscope.

In these figures, oral airway device 100 is shown as an elongate member 102 having a distal end 104 and a proximal end 106. The terms "distal" and "proximal" generally being used as terms relative to a medical professional responsible for handling and inserting of the oral airway device 100 into the mouth of a patient, distal end 104 first. The distal end 104 is generally fully inserted to a point where it is disposed adjacent the patient's tongue root, while the proximal end 106 remains disposed outside the patient mouth. The elongate member 102 is sized for insertion in the mouth of a patient and facilitation of air and medical instrument passage between the proximal end 106 and distal end 104.

The elongate member 102 generally includes a flange assembly 110, a tongue plate 10, a trough 114, and a mandibular flange 6. The flange assembly 110 is located at the proximal end 106 of the elongate member 102 and includes a lower lip flange 2, a pair of upper lip flanges 1, and a sliding insert 3 that removably couples the pair of upper lip flanges 1. At times the pair of upper lip flanges 1 can also alternatively be understood to be collectively referred to as an upper lip flange 1 having a pair of spaced apart lip flange projections. Passageway 4 provides an opening 130 extending through the flange assembly 110 and through the interior of the trough 114. Passageway 4 can be utilized for placement of at least one of an endotracheal tube or flexible fiberoptic endoscope, for example. The pair of upper lip flanges 1 each contains an aperture 59. Apertures 59 can be sized for delivery of oxygen through a nasal oxygen delivery catheter or entry point for a suction catheter during an endoscopic procedure, for example. In some embodiments, lip flanges are provided with holes 59 on one or both sides to deliver oxygen through a nasal oxygen delivery catheter, for use as entry hole for using the suction catheter or introduce washing or other therapeutic agents into the oral cavity through a syringe during flexible fiberoptic endoscopy or while introducing the endotracheal tube on a flexible fiberoptic endoscope.

Sliding insert 3 is generally L-shaped and removable. It has a vertical portion disposed between the upper lip flanges 1 and the horizontal portion disposed over a portion of the trough 114. The sliding insert 3 includes a maxillary engagement surface 134 that defines an upper cover of a passageway 4 that extends into the elongate member 102. Stated differently, removable sliding insert 3 is located between the upper lip flanges 1 and extends backwards to act as a bite block 5. It can easily slide out making the opening communicate with the trough 114 on the tongue plate 10 and to facilitate the removal of the oral airway device 100 with an endotracheal tube and flexible fiberoptic endoscope in the patient's mouth.

The tongue plate 10 extends to the distal end 104 of the elongate member 102. As shown, tongue plate 10 is located at the distal end 104 of the elongate member 102 and provides a curved ventral surface 138 which tapers to a narrow distal edge 140. The curved ventral surface 138 of tongue plate 10 includes a notch 9 and a plurality of transversely disposed ridges 8 shaped to provide downward and inferior tongue pressure on a patient.

Trough 114 extends between the flange assembly 110 and the tongue plate 10. Trough 114 has a generally U-shaped cross-section with a bottom 144 and a pair of vertically extending sidewalls 11 and 12 that taper as they extend distally. Trough 114 provides an upward opening 154 and protection for any medical instruments inserted therein. In general, trough 114 partially surrounds the passageway 4 as it extends through the oral airway device 100 from an opening 120 in the flange assembly 110 to a front middle part 158 of the tongue plate 10.

The mandibular flange 6 projects downwardly and is transversely disposed at a first proximal end 160 of the trough 114. The mandibular flange 6 has a proximally facing surface 130 that is located proximal to the maxillary engagement surface 134 of the sliding insert but distal to the lower lip flange 2.

Embodiments provide a lower jaw thrusting mandibular flange 6. The ventral surface 138 of the tongue plate 10 is provided with horizontal bars 8 and a nub 9 at the distal end to prevent the tongue from moving backwards and to pull the root of the tongue away from the oropharynx to create more space for the flexible fiberoptic endoscope and endotracheal tube advancement.

In some embodiments, oral airway device 100 can be understood to have an elongated body including, a mandibular flange 6 with a lingual flat portion transversely disposed on a ventral surface 138 of a tongue plate 10. The device 100 can have a top part open toward the palate and can have the appearance of a rectangular trough 114 in some embodiments. The trough 114 extends through the device 100 from the proximal end 106 to the front middle part of the tongue plate 10. The device 100 can include an L-shaped plate insert 3 that slideably couples between the right and left upper lip flanges 1 and acts also as dorsal surface of the bite block 5. The distal end 104 of the tongue plate 10 comprises a curved surface which tapers to a narrow distal edge 140. A pair of upstanding walls 11 and 12 attach to the tongue plate ventral surface edges which taper as they extend posteriorly. The walls 11 and 12 ensure protection for medical instruments disposed within the flexible fiberoptic endoscope guide.

Figure 2:
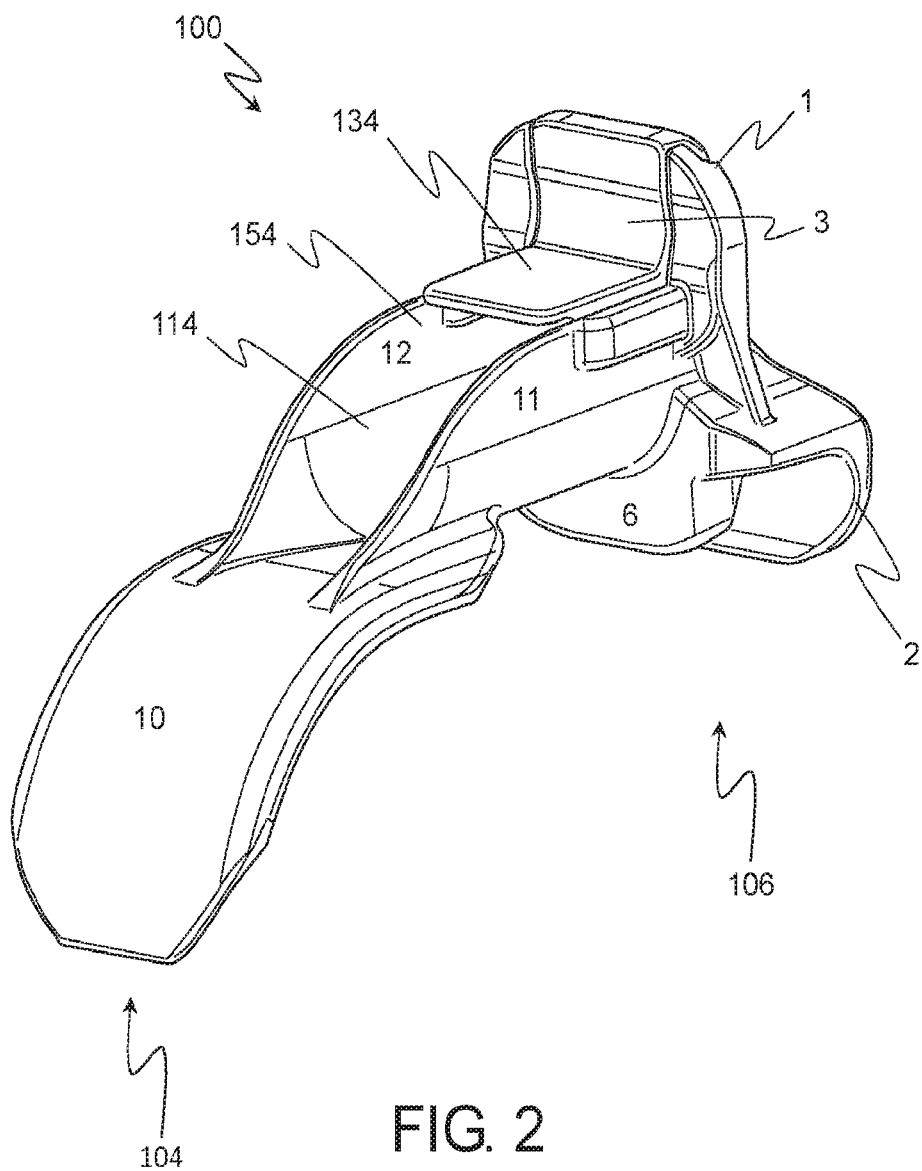
FIG. 2 is a rear perspective view of an LJT-ET-FO oral airway device, according to an embodiment.

FIG. 1 shows oral airway device 100 from a front perspective view and FIG. 2 shows oral airway device 100 from a rear perspective view.

Figure 3A:
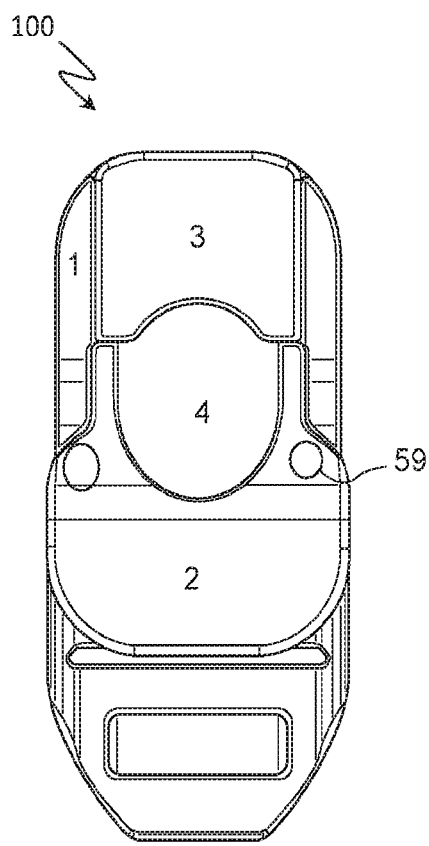
FIG. 3A is a front view of an LJT-ET-FO oral airway device, according to an embodiment.

FIG. 3A shows a front view of oral airway device 100 in which the oval opening 130 is partially defined by sliding insert 3. As shown, lip flange 1 and lower lip flange 2 can be understood to surround an opening 130 and passageway 4 to facilitate the use of a flexible fiberoptic endoscope and endotracheal tube insertion. Sliding insert door 3 can be removed from its position in FIG. 3A to make an opening on the upper surface of the airway cavity all the way on the tongue plate 10 to facilitate a procedure, and the removal of the oral airway device 100 entirely, if needed, with ease. Removal of the sliding insert door 3 opens up the entire dorsal surface to the palate and upper jaw.

Figure 3B:
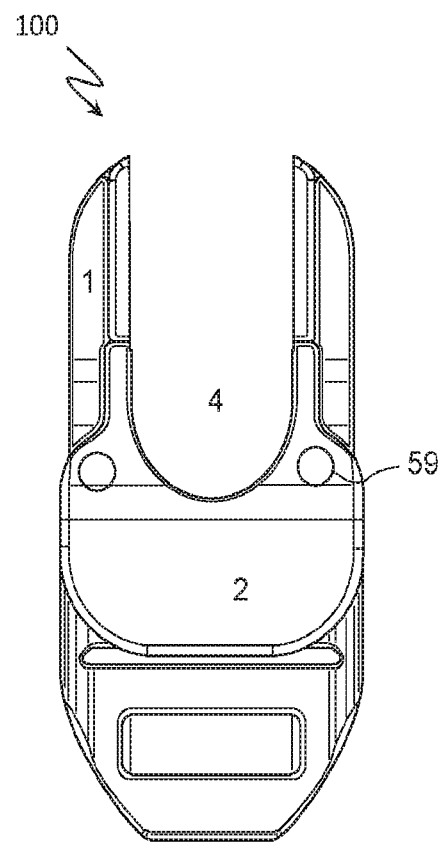
FIG. 3B is a front view of an LJT-ET-FO oral airway device where the L-shaped insert has been removed, according to an embodiment.

More specifically, FIG. 3B shows a front view of oral airway device 100 in which the sliding insert 3 is removed. Upper lip flanges 1 comprise two pillars defining the sides of the opening. In this configuration, the upper surface of the oral airway device 100 is open all the way along the tongue plate 10. This configuration facilitates easy placement of a flexible fiberoptic endoscope and endotracheal tube. Further, removal of the oral airway device 100 is done with ease, if needed, with an inserted flexible fiberoptic endoscope and endotracheal tube left in place.

Figure 4:
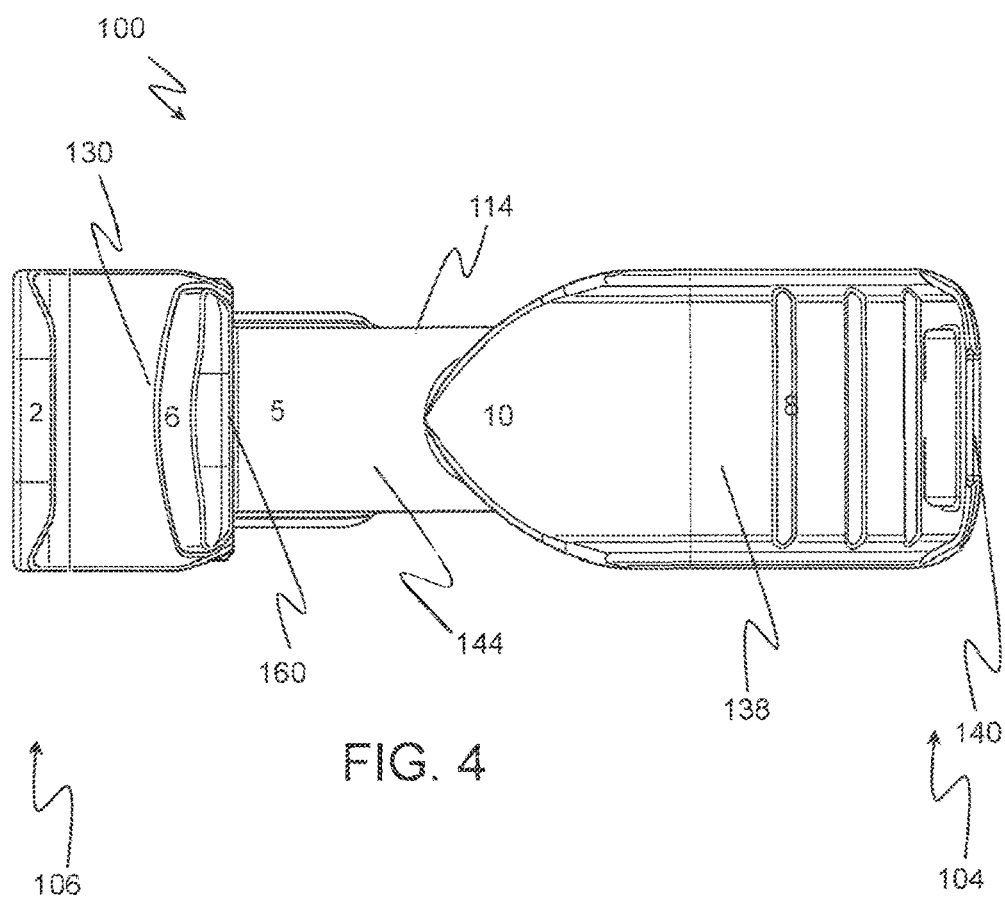
FIG. 4 is a bottom view of an LJT-ET-FO oral airway device, according to an embodiment.
Figure 5:
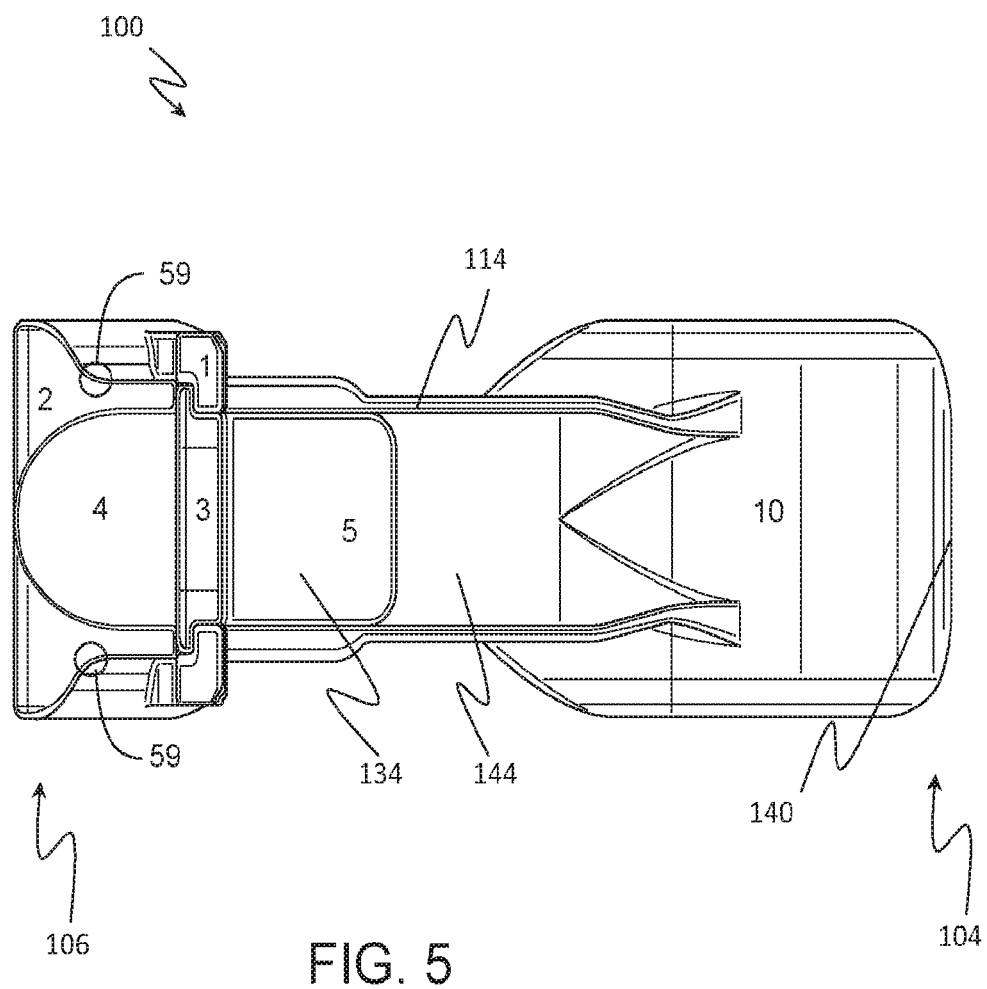
FIG. 5 is a top view of an LJT-ET-FO oral airway device, according to an embodiment.

FIG. 4 shows a bottom view of oral airway device 100 in which the ventral surface can be seen and FIG. 5 shows a top view of oral airway device 100 in which the dorsal surface and front can be seen.

Figure 6:
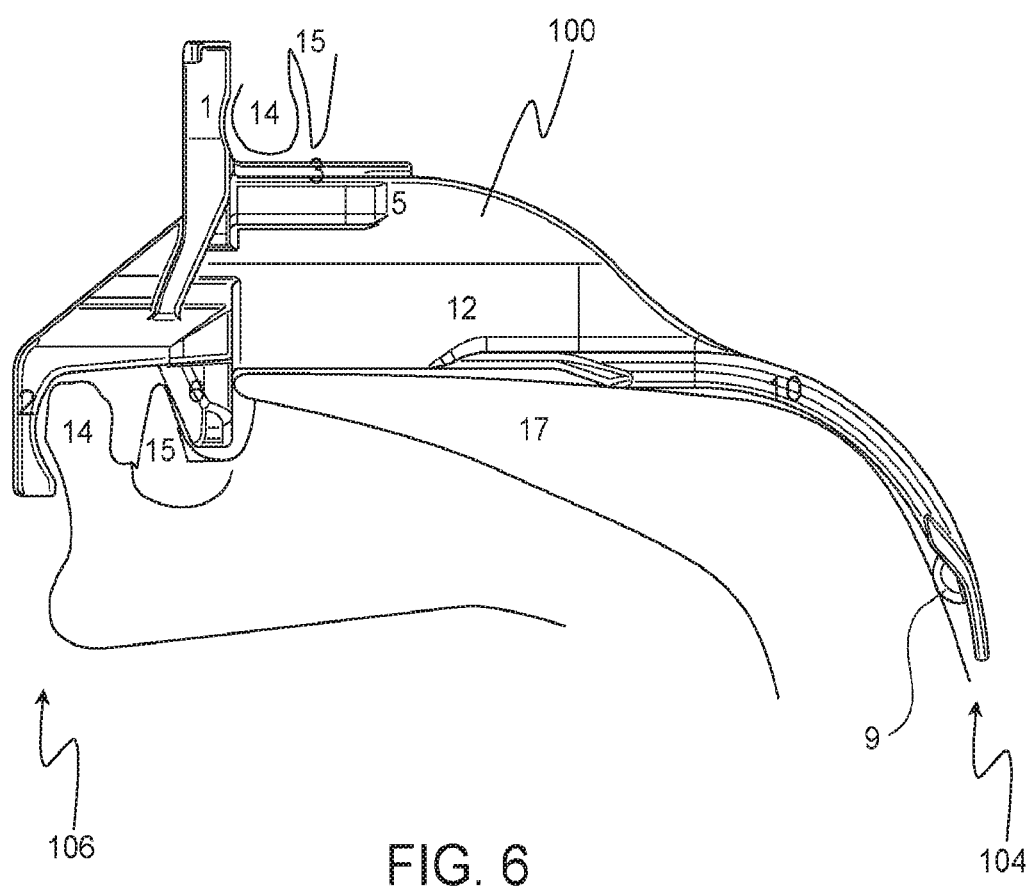
FIG. 6 is a side view of an LJT-ET-FO oral airway device positioned in a cross-sectional view of a mouth with maxillary and mandibular incisor teeth in position, according to an embodiment.

FIG. 6 shows side view of oral airway device 100 positioned in a cross-sectional view of a mouth with maxillary and mandibular incisor teeth 15 and lips 14 in position. The lower jaw is thrust with the tongue and the ventral surface of the bite block. The ventral surface of the bite block 5 angles inferiorly towards the lower front lip flange 2 to better hold the mandibular teeth and jaw protracted in an anesthetized patient, which is caused by the flaccid jaw muscles being relaxed to allow the jaw to fall away and downward from the jaw plane.

The lower jaw is thrust with the tongue 17 widening part on the dorsal surface of the oral cavity, thus the oral cavity and oropharynx are wide open to facilitate the use of flexible fiberoptic endoscope for diagnosis and treatment as well as endotracheal tube insertion.

Figure 7:
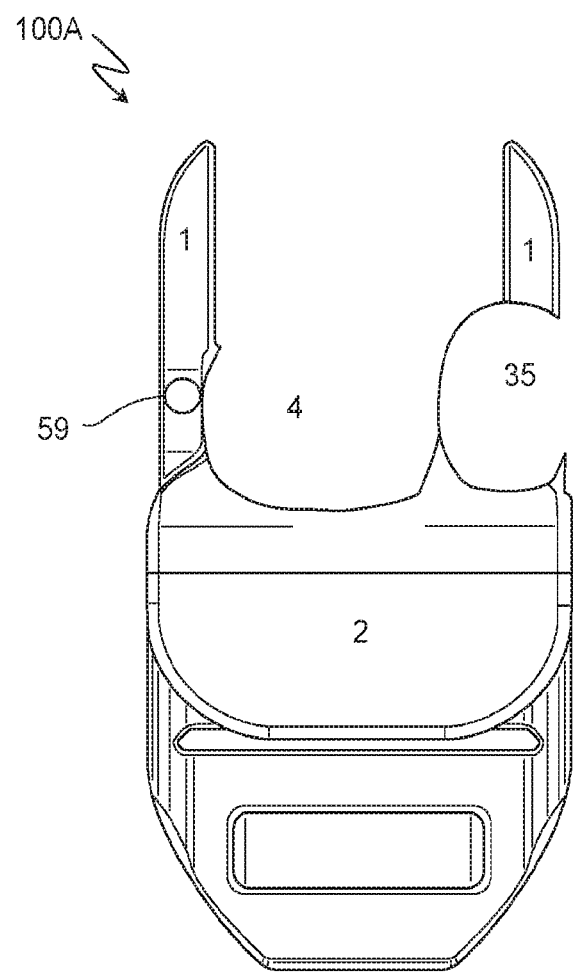
FIG. 7 is a front view of an LJT-ET-FO oral airway device, according to an alternate embodiment.

FIG. 7 shows a front view of an alternate embodiment depicting an oral airway device 100A. Oral airway device 100A of FIG. 7 can be viewed in contrast to the similar view of oral airway device 100 in FIG. 3B, for example. Oral airway device 100 shows a device having front and side portions including passageways 4 and 35. Passageway 4 is for use with a flexible fiberoptic endoscope and the passageway 35 is used to accommodate a laryngeal mask airway.

Figure 8:
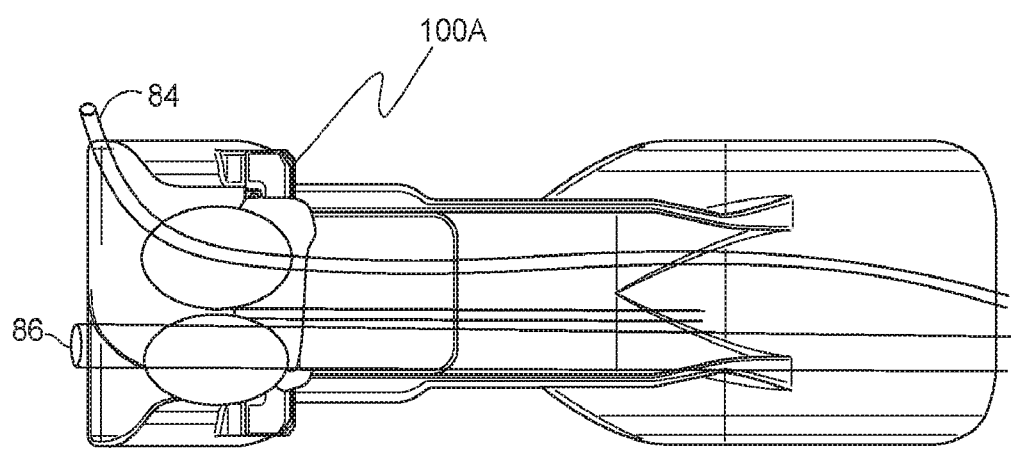
FIG. 8 is a diagram view showing the general locations of a flexible fiberoptic endoscope and a laryngeal mask airway passing through an an LJT-ET-FO oral airway device, according to an alternate embodiment.

FIG. 8 shows an oral airway device 100A with a flexible fiberoptic endoscope 84 and laryngeal mask airway 86 in position.

In general, embodiments of the oral airway device 100 can be differentiated from other devices in various ways and based on various features. One potentially differentiating feature is the lower jaw and tongue thrusting design of the oral airway device 100. Another is that the oral airway device 100 has no central directing endotracheal tongs, like those in Ovassapian oral airway devices. This configuration facilitates the sliding to place flexible fiberoptic endoscope and endotracheal tubes with inflating balloons with ease. Further, the oral airway device 100 includes transverse bars on the ventral surface of the tongue plate to prevent the movement of the tongue from side-to-side and backwards. Similarly, a ventral nub is provided to pull the root of the tongue away from epiglottis, thus opening up the oropharynx and laryngeal opening and allowing easy visualization of the laryngeal and esophageal opening by the distal end of the flexible fiberoptic endoscope for intubation and EGD procedures.

Oral airway devices 100 have a well-defined sliding plate that acts as bite bock and completes as an oral airway in the traditional way. This plate can be removed from the upper lip flange to facilitate the flexible fiberoptic endoscope and endotracheal tube introduction and removal of the oral airway from the mouth with the flexible fiberoptic endoscope and endotracheal tube still inside the mouth.

In various embodiments, features of the oral airway device 100 can include that it: Facilitates fiberoptic scopes placement with ease; Facilitates flexible fiberoptic endoscope endotracheal tube placement to trachea without obstacle at the site of balloon; Allows the placement of IMA if needed; Allows easy ventilation by using Mask and thus prevents bloating of the stomach with ventilated air with mask ventilation; Prevents the movement of the tongue on the endotracheal tube or flexible fiberoptic endoscope and backwards on the oropharynx; Can be an alternative to a LMA in short duration anesthesia cases; Provides a bite block insert that can be removed and replaced as needed; increases air-oxygen flow to oropharynx then to larynx-lungs instead of into the stomach; Facilitates its use in obese and overweight patients for flexible fiberoptic endoscope and endotracheal tube placements and has advantages in pediatric patients also; Can be use with or without muscle relaxants in conscious, semiconscious/unconscious states, under topical anesthesia and cardiac arrest or CPR; is better than face mask only designs and need not protrude the jaw from the angle of the jaw with its use; permits hands are free to attend to other patient needs; can be used for fiberoptic intubation; can provide a good seal at peak inspiratory pressure with mask and/or extension attachment attached to Ambu hag or mechanical ventilators; has an aspiration risk that is the same as a LMA and is reduced considerably due to opening of the oral and oropharynx air passage; provides easy entry of air to tracheobronchial tree instead of the esophageal opening; provides minimal mucosal trauma after use due to reduced movement of the tongue; is generally better than LMA that replaces endotracheal intubation during emergency CPR by paramedics, especially in pediatric patients and for household use; provides the opportunity to convert to a definitive airway after rescue with the supraglottic device; and does not require a manual jaw-thrust by using both hands while transporting patients to the recovery room after surgery due to the mandibular flange holding the lower jaw and tongue protracted.

In some embodiments, an oral airway device 100 (or variations 100A, . . . ) may be adapted, configured, or manufactured to provide a desirable smell and/or taste with a coating, a flavoring material such as food, a natural flavor, or an artificial flavor including, but not limited to, bubble gum or a fruit, such as an orange may be applied during the manufacture or after of an oral airway device, that results in a desirable pleasing flavor being experienced when the oral airway is utilized in the mouth. The scent or odor may be that of a food or other pleasant item with color coating for particular taste and smell. It will be apparent to those of ordinary skill in the art that several modifications, including, but not limited to, variations in size, materials, shape, color are contemplated. Further, additions of tasting and smelling aspects to the form, function, manner of procedure, assembly and use are contemplated.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

What is claimed is:

1. A lower jaw and tongue thrusting endotracheal tube and flexible fiberoptic endoscope intubation (LJT-ET-FO) oral airway device, comprising
    an elongate member having a distal end and a proximal end, the elongate member sized for insertion in the mouth of a patient and facilitation of air and medical instrument passage between the proximal and distal ends, including:
        a flange assembly located at the proximal end of the elongate member including a lower lip flange, a pair of upper lip flanges, and a sliding insert that removably couples the pair of upper lip flanges, the sliding insert including a maxillary engagement surface that defines an upper cover of a passageway extending into the elongate member;
        a tongue plate extending to the distal end of the elongate member;
        a trough extending between the flange assembly and the tongue plate;
        a mandibular flange projecting downwardly and transversely disposed at a first proximal end of the trough;
        wherein the mandibular flange has a proximally facing surface that is located proximal to the maxillary engagement surface of the sliding insert but distal to the lower lip flange.

2. The oral airway device of claim 1, wherein the trough has a generally U-shaped cross section with a bottom and a pair of vertically extending sidewalls that taper as they extend distally, the trough providing an upward opening and protection for any medical instruments inserted therein.

3. The oral airway device of claim 2, wherein the trough partially surrounds the passageway as it extends through the device from an opening in the flange assembly to a front middle part of the tongue plate.

4. The oral airway device of claim 1, wherein the passageway provides an opening extending through the flange assembly and through the interior of the trough for placement of at least one of: an endotracheal tube; and flexible fiberoptic endoscope.

5. The oral airway device of claim 1, wherein the sliding insert is generally L-shaped.

6. The oral airway device of claim 1, wherein the tongue plate at the distal end of the elongate member provides a curved surface which tapers to a narrow distal edge.

7. The oral airway device of claim 1, wherein the tongue plate has a curved ventral surface including a notch and a plurality of transversely disposed ridges shaped to provide downward and inferior tongue pressure on the patient.

8. The oral airway device of claim 1, wherein at least one of the pair of upper lip flanges contains an aperture.

9. The oral airway device of claim 8, wherein the aperture is sized for delivery of oxygen through a nasal oxygen delivery catheter or entry point for a suction catheter during an endoscopic procedure.

10. A lower jaw and tongue thrusting endotracheal tube and flexible fiberoptic endoscope intubation (LJT-ET-FO) oral airway device, comprising:
    a semi-rigid, semi-rectangular, elongate member with two lateral walls extending from a flat ventral base with an open top lumen, the elongate member extending from a proximal end that includes an upper lip flange, a lower lip flange, and a bite block to a distal end having structure for location adjacent the root of the tongue of a patient including a tongue plate;
    wherein the bite block partially defines a passageway between a pair of spaced apart lip flange projections that comprise the upper lip flange and the lower lip flange;
    wherein the bite block has a ventral surface with a mandibular flange in vertical alignment with the upper lip flange but distal to the lower lip flange, the mandibular flange configured to be placed behind mandibular incisor teeth of the patient to hold the lower mandibular jaw and the tongue of the patient as the lower jaw is thrust forward into position;
    wherein the bite block has a resilient, teeth and lip engaging part on the ventral surface between the lower lip flange and the mandibular flange for placing lower incisor teeth and lower lip for maintaining a protracted mandibular position; and
    wherein the ventral surface of the bite block angles inferiorly towards the lower lip flange.

11. The oral airway device of claim 10, wherein the passageway between the upper lip flange is covered by a sliding insert which is removably coupled between the pair of lip flange projections of the upper lip flange, and extends backwards with a dorsal surface for engagement by maxillary teeth, the sliding insert configured to be easily removed to facilitate removal of the oral airway device.

12. The oral airway device of claim 11, wherein one of the lateral walls and upper lip flange include an aperture to hold a laryngeal mask airway (LMA) in position during flexible fiberoptic endoscope procedures to maintain oxygenation and air movement.

13. The oral airway device of claim 10, wherein a plurality of transverse ridges are included on a ventral surface of the tongue plate that is configured to position and maintain the tongue of the patient in a forward position.

14. The oral airway device of claim 10, wherein a nub is provided on a ventral surface at the end of the tongue plate and configured to prevent the movement of the tongue on the epiglottis by pulling the root of the tongue away from a epiglottis.

15. The oral airway device of claim 10, wherein the tongue plate is large, curved and includes a plurality of transverse bars configured to prevent the movement of the tongue from side to side and backwards during the flexible fiberoptic endoscope and endotracheal tube placement procedures.

16. The oral airway device of claim 10, wherein the oral airway device includes a generally flat open end and a trough through which a flexible fiberoptic endoscope and an endotracheal tube can be placed, thus permitting manipulation of a tip of an inserted medical instrument.

\* \* \* \* \*